United States Patent [19]

Anderson et al.

[11] Patent Number: 5,767,335
[45] Date of Patent: Jun. 16, 1998

[54] METHOD FOR PREVENTING THE ACCUMULATION OF LIGHT ASO IN THE ALKYLATION CATALYST OF ALKYLATION PROCESS SYSTEM

[75] Inventors: Richard L. Anderson; Keith W. Hovis, both of Bartlesville, Okla.

[73] Assignee: Phillips Petroleum Company, Bartlesville, Okla.

[21] Appl. No.: 574,170

[22] Filed: Dec. 18, 1995

[51] Int. Cl.$^6$ .................................................. C07C 2/58
[52] U.S. Cl. .................... 585/723; 585/724; 585/719; 585/730; 208/133; 208/134
[58] Field of Search ........................ 585/723, 724, 585/719, 730; 208/133, 134

[56] References Cited

U.S. PATENT DOCUMENTS

| | | | |
|---|---|---|---|
| 3,749,753 | 7/1973 | Skraba | 260/683.48 |
| 3,871,969 | 3/1975 | Chapman | 202/234 |
| 3,919,343 | 11/1975 | Sobel et al. | 260/683.48 |
| 3,925,318 | 12/1975 | Parker et al. | 260/683.58 |
| 3,956,416 | 5/1976 | Vora | 260/683.48 |
| 3,972,956 | 8/1976 | Carter | 260/683.48 |
| 4,199,409 | 4/1980 | Skraba | 203/39 |
| 4,237,327 | 12/1980 | Winter, III | 585/450 |
| 4,316,998 | 2/1982 | Van Pool | 585/712 |
| 4,513,165 | 4/1985 | Van Pool | 585/723 |
| 5,264,652 | 11/1993 | Child et al. | 585/723 |
| 5,336,832 | 8/1994 | Keller | 585/710 |
| 5,382,746 | 1/1995 | Child et al. | 585/802 |
| 5,547,909 | 8/1996 | Carlson | 502/20 |

*Primary Examiner*—Walter D. Griffin
*Assistant Examiner*—Nadine Preisch
*Attorney, Agent, or Firm*—Charles W. Stewart

[57] ABSTRACT

Disclosed is an alkylation process which utilizes a mixture of sulfone and hydrogen fluoride as an alkylation catalyst. The process provides for the removal of light ASO from the alkylation catalyst that accumulates therein as a result of the inability to remove the light ASO produced as a by-product of the alkylation reaction.

7 Claims, 1 Drawing Sheet

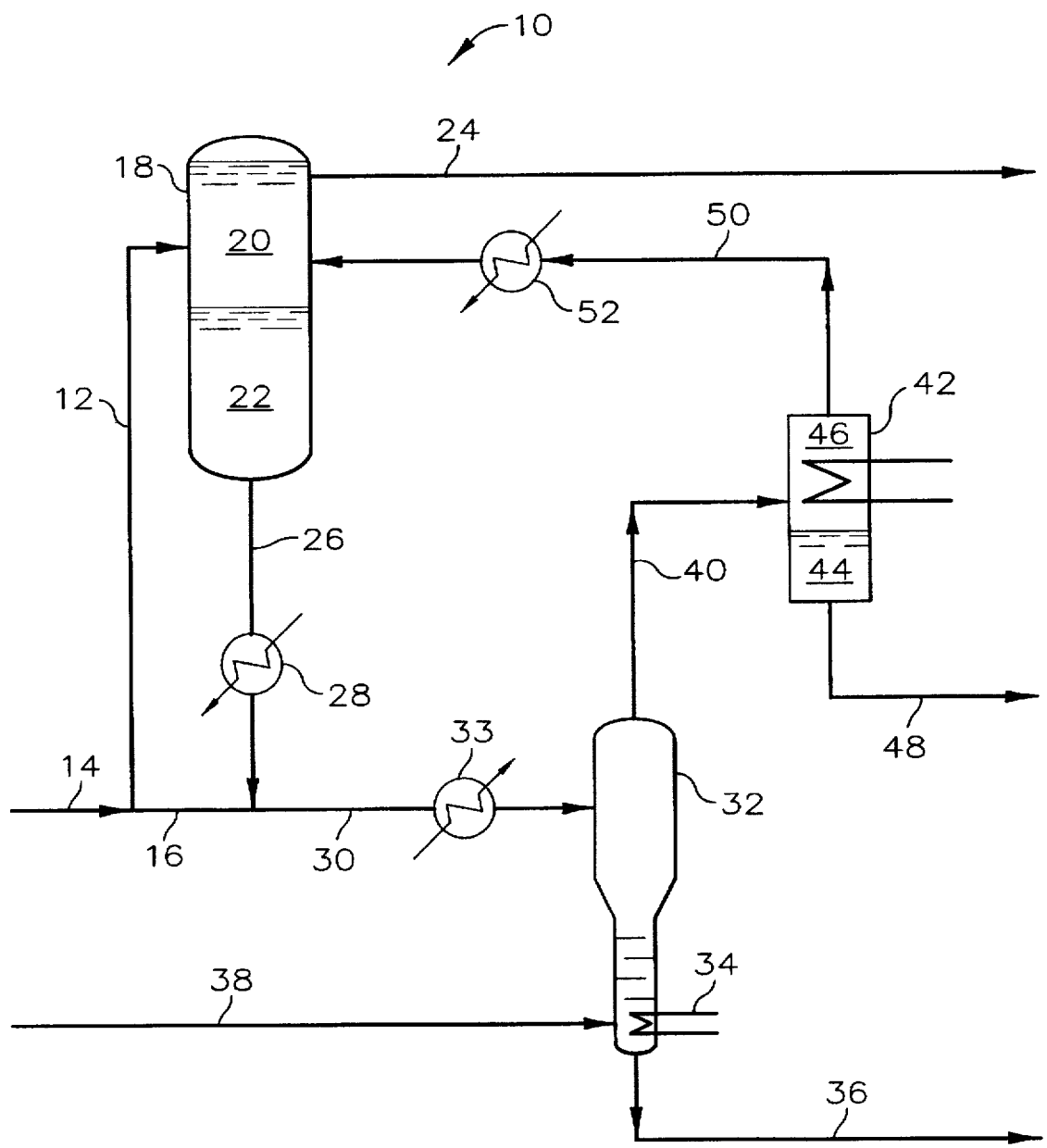

5,767,335

METHOD FOR PREVENTING THE ACCUMULATION OF LIGHT ASO IN THE ALKYLATION CATALYST OF ALKYLATION PROCESS SYSTEM

The present invention relates to a hydrocarbon conversion process for the alkylation of olefin hydrocarbons by isoparaffin hydrocarbons which utilizes a catalyst mixture comprising a sulfone compound and a hydrogen halide compound. More specifically, the invention relates to a process for removing acid soluble oil from an alkylation catalyst used in an alkylation process system to prevent buildup therein.

BACKGROUND OF THE INVENTION

It has recently been discovered that a mixture, comprising a sulfone compound and a hydrogen halide compound, can be an effective catalyst for use in the alkylation of olefin hydrocarbons by isoparaffin hydrocarbons to produce an alkylate reaction product, or alkylate. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain unwanted polymeric reaction by-products such as those referred to as acid-soluble oils, or ASO. These polymeric reaction by-products are referred to as acid-soluble oils; because, they are soluble in the acid catalyst utilized in the alkylation process and, thus, remain in the acid catalyst phase when the alkylate product resulting from the contact of a hydrocarbon mixture with an alkylation catalyst is separated from the alkylation catalyst.

In an alkylation process which continuously separates the catalyst phase from the alkylation reaction product for reuse in the process reaction zone, there is a buildup of ASO in the catalyst phase. Over time, the ASO concentration will reach unacceptable concentration levels if not removed. A low concentration of ASO in the alkylation catalyst comprising a sulfone component and a hydrogen halide component is believed to have a beneficial effect upon the alkylation process or its product. However, a higher concentration of ASO in the alkylation catalyst has an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in the alkylate octane.

In conventional alkylation processes that use a substantially pure hydrogen fluoride material as a catalyst, as opposed to the use of the aforementioned catalyst mixture comprising a sulfone component and a hydrogen halide component, there are certain known methods for removing the ASO from the HF catalyst used in a continuous alkylation process. This is generally done by passing a portion of the HF catalyst to a stripping vessel whereby the HF is stripped from the ASO by means of a vaporous hydrocarbon such as isobutane.

In processes that utilize an alkylation catalyst containing both a sulfone component and hydrogen halide component, the aforementioned means for separating or removing ASO by-product from the alkylation catalyst has been found to be unsuitable due to the inability to remove the lighter boiling acid soluble oils from the alkylation catalyst. It has been found that due to the operating temperature of a typical stripping means, the lighter boiling ASO of the ASO by-product will pass with the stripper overhead rather than with the stripper bottoms product. The stripper overhead from the stripping means is conventionally returned back to the alkylation catalyst for reuse in the alkylation reaction system. But, with the nonconventional alkylation process, which utilizes the sulfone and HF alkylation catalyst, return of the stripper overhead to the alkylation catalyst cannot effectively be done due to the resultant accumulation of light ASO in the alkylation catalyst.

SUMMARY OF THE INVENTION

It is, therefore, an object of this invention to provide a novel method for removing ASO from a sulfone and hydrogen fluoride alkylation catalyst.

A further object of this invention is to provide a method for preventing the accumulation of ASO within an alkylation catalyst of a continuous alkylation process.

A still further object of this invention is to provide a method for removing the light ASO portion of the ASO by-product from an alkylation catalyst comprising a sulfone, hydrogen halide and ASO and reusing the resultant product as an alkylation catalyst.

Thus, the present invention relates to a method for preventing the accumulation of light ASO within an alkylation catalyst of an alkylation process system. This method includes alkylating an isoparaffin with an olefin in the presence of an alkylation catalyst, which contains HF and sulfone, in an alkylation reaction zone to thereby form an alkylate product and an ASO reaction by-product. The ASO reaction by-product contains a light ASO component and a heavy ASO component. The alkylation reaction zone effluent contains the alkylate product and the ASO reaction by-product and is passed to separation means whereby the alkylation reaction zone effluent is separated into a hydrocarbon phase containing the alkylate product and an alkylation catalyst phase containing the alkylation catalyst and the ASO reaction by-product. A portion of the alkylation catalyst phase is passed to a stripping vessel for stripping hydrogen fluoride therefrom to provide a stripper bottoms stream and a stripper overhead stream. The stripper bottoms stream contains heavy ASO, and the stripper overhead stream contains hydrogen fluoride, light ASO and is substantially in the vapor state. An important aspect of the invention includes the partial condensation of the stripper overhead stream to form two separate phases: a liquid phase containing light ASO and a vapor phase containing a hydrogen fluoride. The vapor phase can be reused by combining it with the alkylation catalyst phase and the liquid phase containing light ASO can be removed from the alkylation process system by passing it downstream for further processing or disposal.

BRIEF DESCRIPTION OF THE DRAWING

The accompanying drawing is a schematic representation of the process which is one embodiment of the invention.

Other objects and advantages of the invention will be apparent from the detailed description of the invention and the appended claims.

DETAILED DESCRIPTION OF THE INVENTION

The acid soluble oil referred to herein is produced as a reaction by-product in an alkylation process comprising the step of contacting a hydrocarbon mixture, which comprises olefins and isoparaffins, with an alkylation catalyst, which comprises a hydrogen halide component and a sulfone component. As used within this description and in the appended claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1, (January 1963) by Miron and Lee. This article is incorporated herein by reference.

The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is more narrowly defined, ASO will be those conjunct polymers produced as a by-product in the catalyzed reaction of mono-olefins with isoparaffins utilizing a catalyst mixture comprising a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane and the preferred hydrogen halide component is hydrogen fluoride.

The ASO by-product derived from the hydrocarbon reaction catalyzed by a sulfone-containing alkylation catalyst can be further generally characterized as having a specific gravity, with water at 60° F. as the reference, in the range of from about 0.8 to about 1.0, an average molecular weight in the range of from about 250 to about 350, and a bromine number in the range of from about 40 to about 350. The boiling temperature of the ASO by-product can range from an initial boiling point of about 150° F. to an end-point of about 1100° F. This ASO by-product includes a light ASO portion and a heavy ASO portion. The term "light ASO", as used in this description and in the appended claims, refers to an ASO by-product having a boiling temperature less than 300° F. The term "heavy ASO", as used in this description and in the appended claims, refers to an ASO by-product having a boiling temperature greater than 300° F. Thus, a light ASO can have a boiling temperature in the range of from 150° F. to 300° F., and a heavy ASO can have a boiling temperature in the range of from 300° F. to 1100° F.

The hydrogen halide component of the alkylation catalyst composition or alkylation catalyst mixture utilized in the alkylation process can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water.

The sulfones suitable for use in this invention are the sulfones of the general formula

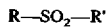

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethyl-sulfone and the alicyclic sulfones wherein the SO group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as, for example, chloromethylethylsulfone. These sulfones may advantageously be used in the form of mixtures.

When sulfolane is used as the preferred sulfone, it can be utilized in the alkylation catalyst composition in anhydrous form, but, more often, the sulfolane component, when added to the alkylation catalyst composition as a make-up component, can have a small amount of water. Generally, the sulfolane component used to form the alkylation catalyst mixture will have a water concentration up to about 5 weight percent of the total weight of the sulfolane and water. However, preferably, the water contained in the sulfolane component will be in the range of from about 0.1 to about 5.0 weight percent of the total weight of the sulfolane and water and, most preferably, the water will be present in the range of from 0.5 to 4 weight percent.

In the alkylation process, the accumulation of water in the alkylation catalyst composition, which comprises hydrogen fluoride and sulfolane, in no event can be more than about 10 weight percent of the total weight of the catalyst composition, which includes sulfone, hydrogen halide and water. Preferably, the concentration of water present in the alkylation catalyst composition is less than about 7.5 weight percent. Most preferably, the concentration of water present in the alkylation catalyst composition is less than 3 weight percent.

Thus, the alkylation catalyst composition used in the alkylation process system wherein an ASO reaction by-product is produced can comprise a hydrogen halide component and a sulfone component, both as described herein, and a concentration of water. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with a weight ratio of hydrogen fluoride to sulfolane in the alkylation catalyst in the range of from about 1:1 to about 40:1. A preferred weight ratio of hydrogen fluoride to sulfolane can range from about 1.2:1 to about 19:1 and, more preferably, it can range from 1.5:1 to 9:1.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-into-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

In the alkylation process, the reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. A portion of the catalyst can continuously be regenerated or reactivated as described herein, or by any other suitable treatment, and returned to the alkylation reactor.

To regenerate the alkylation catalyst, at least a portion of the alkylation catalyst of the alkylation reaction system is passed to a stripping vessel for separating at least a portion of alkylation catalyst into a stripper overhead stream and a stripper bottoms stream. This portion of the alkylation catalyst can also be referred to as a slip stream. This slip stream contains the hydrogen fluoride and sulfone catalyst mixture along with a concentration of the ASO by-product and water which have accumulated in the alkylation catalyst.

It is important to the proper operation of the alkylation reaction process to maintain a reasonably low concentration of acid soluble oil in the alkylation catalyst. Thus, the ASO concentration should not exceed 10 weight percent of the alkylation catalyst. Preferably, the ASO concentration is less than 7.5 weight percent and, most preferably, the ASO concentration is less than 5 weight percent. Thus, the ASO concentration will generally be in the range of 0.25 weight percent to 10 weight percent, but specifically, it can be in the range from 0.5 weight percent to 7.5 weight percent. More specifically, it will be in the range from 0.75 weight percent to 5 weight percent.

The slip stream is passed or charged to a stripping column, which defines a separation zone and provides means for separating the alkylation catalyst into a stripper bottoms stream containing heavy ASO and a stripper overhead stream containing hydrogen fluoride and light ASO. It is preferred for the stripping means to be a standard separation column which utilizes hot vaporous isobutane as a stripping fluid.

The bottoms stream from the stripping column contains sulfone, is rich in heavy ASO and, preferably, contains less than 20 weight percent HF. The overhead stream of the stripping column is a vaporous product containing hydrogen fluoride, light ASO and water. It is a critical aspect of this invention that the vaporous overhead stream passes to a condenser that only partially condenses the vaporous overhead stream to form at least two phases, one of which is a liquid phase and the other is a vapor phase. The liquid phase of the partial condenser contains water, is rich in light ASO and, preferably, contains less than 50 weight percent HF and, most preferably, less than 25 weight percent HF. The vapor phase of the partial condenser contains hydrogen fluoride, isobutane and less than 5 weight percent light ASO. Preferably, the vapor phase is substantially free of light ASO.

The importance of the partial condensation step is that, by only partially condensing the vaporous overhead from the stripping column, the light ASO and water can be removed from the alkylation process system; because, they are the primary components condensed. The hydrogen fluoride remains predominantly in a vaporous state and can be recycled back to and reused as an alkylation catalyst in an alkylation process system. If the vaporous overhead stream from the stripping column were not subject to a partial condensation prior to recycling the hydrogen fluoride back to the alkylation catalyst, the light ASO would remain therein and undesirably accumulate within the alkylation catalyst. Thus, the uncondensed vapor of the vaporous overhead stream from the stripping column can be reused as a part of the alkylation catalyst of an alkylation process system, optionally, being condensed prior to mixing therewith.

The liquid phase of the partial condenser contains a substantial fraction of the water and light ASO contained in the slip stream charged to the stripping column. This permits the dual benefit of removing not only the light ASO from the alkylation catalyst but also water which is also accumulated in the alkylation catalyst.

The bottoms stream from the stripping column primarily contains sulfone and heavy ASO. The sulfone component of the bottoms stream represents at least 90 percent of the sulfone contained in the slip stream charged to the stripping column. Preferably, the sulfone in the bottoms stream will contain at least 95 percent of the sulfone in the slip stream feed and, most preferably, it will represent at least 99 percent of the sulfone in the slip stream feed. This bottoms stream is rich in heavy ASO generally containing 90 percent of such heavy ASO contained in the slip stream. Preferably, the ASO contained in the bottoms stream is 95 percent of the heavy ASO contained in the slip stream.

Now referring to the drawing, there is depicted by schematic representation an alkylation process system 10. A hydrocarbon feed mixture, comprising olefins and isoparaffins, is introduced into riser-reactor 12 through conduit 14. Riser-reactor 12 defines a reaction zone wherein the hydrocarbon feed mixture is contacted, or admixed, with an alkylation catalyst mixture, comprising sulfolane, water, and hydrogen fluoride, in order to produce a reaction product and a reaction by-product. The olefins of the hydrocarbon feed mixture generally comprise one or more olefins having from three to five carbon atoms, and the isoparaffins of the hydrocarbon feed mixture generally will have from four to six carbon atoms. The alkylation catalyst mixture is introduced into riser-reactor 12 via conduit 16.

The admixture of hydrocarbon feed mixture and alkylation catalyst mixture passes through the reaction zone defined by riser-reactor 12 wherein a reaction takes place in which the olefins of the hydrocarbon feed mixture react with isoparaffins of the hydrocarbon feed mixture to produce an alkylate reaction product. Also, within the reaction zone, the alkylation reaction by-product, ASO, is formed.

The reactor effluent, which includes the reaction product and reaction by-product, from riser-reactor 12 passes to settler vessel 18, which defines a separation zone for separating the alkylate reaction product from the alkylation catalyst mixture to produce a separated reaction product 20 and a separated alkylation catalyst phase 22. The separated alkylation catalyst phase 22 will contain a portion, but, preferably, a substantial portion, of the alkylation reaction by-product, ASO. The separated reaction product 20 passes to downstream processing via conduit 24. The separated alkylation catalyst phase 22 can be recycled via conduits 26 and 16 to riser-reactor 12 for reuse as the alkylation catalyst mixture. Interposed in conduit 26 is catalyst cooler 28, which defines a heat transfer zone for exchanging heat from separated alkylation catalyst phase 22 to a heat transfer fluid such as water.

In order to regenerate the separated alkylation catalyst phase by removing accumulated ASO and water, a portion, sometimes referred to as a slip stream or a drag stream, of the separated alkylation catalyst phase 22 passes by way of conduit 30 to stripping column 32. Interposed in conduit 30 is heater 33, which defines a heat transfer zone and provides means for heating the slip stream, preferably, to vaporize at least a portion of the slip stream such as the lights material contained in the acid phase.

Stripping column 32 may be equipped with reboiler 34 and defines a separation zone for separating the slip stream of separated alkylation catalyst phase 22 into at least two streams: (1) a stripper overhead stream, comprising a portion of the hydrogen fluoride and light ASO contained in the slip stream, and (2) a stripper bottoms stream, comprising a portion of the sulfolane component of the slip stream. The stripper bottoms stream will also contain a portion, preferably a substantial portion, of the heavy ASO contained in the slip stream. The stripper bottoms stream passes from stripping column 32 by way of conduit 36.

Introduced into stripping column 32 by way of conduit 38 is vaporous isobutane which provides energy for separating the slip stream into the stripper overhead stream and the stripper bottoms stream and, more specifically, for stripping the hydrogen fluoride from the slip stream. The stripper overhead stream, which is in a vaporous state, passes by way of conduit 40 to partial condenser 42, which defines a heat transfer zone and provides means for removing heat energy from the stripper overhead stream and for partially condensing the stripper overhead stream. An important aspect of the inventive process is that the stripper overhead stream only be partially condensed; since, it is desirable to only condense the light ASO and water so as to remove them from the stripper overhead stream without removing a significant amount of HF.

Thus, partial condenser 42 provides for the formation of a liquid phase 44, containing light ASO and, preferably, water, and vapor phase 46, containing hydrogen fluoride that is preferably substantially free of light ASO. The vapor phase also can contain the isobutane stripping gas. The liquid phase will pass from partial condenser 42 by way of conduit 48 thereby removing from the alkylation process system 10 light ASO to thus prevent the accumulation thereof in the separated alkylation catalyst phase 22 when the recovered hydrogen fluoride is recycled or recombined therewith. The vapor phase 46 can pass by way of conduit 50 to settler vessel 18 wherein it is recombined with the separated alkylation catalyst phase 22. Optionally, interposed in conduit 50 is condenser 52, which defines a heat transfer zone and provides means for removing heat from the vapor phase 46. Condenser 52 can optionally condense vapor phase 46 prior to passing the thus condensed vapor phase to settler vessel 18.

While this invention has been described in terms of the presently preferred embodiment, reasonable variations and modifications are possible by those skilled in the art. Such variations and modifications are within the scope of the described invention and the appended claims.

That which is claimed is:

1. A method for preventing the accumulation of light ASO within an alkylation catalyst system, said method comprises the steps of:

alkylating an isoparaffin with an olefin in the presence of an alkylation catalyst mixture, containing hydrogen fluoride ("HF") and sulfone, in an alkylation reaction zone thereby forming an alkylate product and an ASO reaction by-product containing light ASO and heavy ASO;

passing an alkylation reaction zone effluent, containing said alkylate product and said ASO reaction by-product, from said alkylation reaction zone to a separation zone for separating said alkylation reaction zone effluent into a hydrocarbon phase, containing said alkylate product, and an alkylation catalyst phase, containing said alkylation catalyst mixture and said ASO reaction by-product;

passing at least a portion of said alkylation catalyst phase to means for stripping HF from said at least a portion of said alkylation catalyst phase to provide a stripper bottoms stream and a stripper overhead stream, said stripper bottoms stream contains heavy ASO and said stripper overhead stream is substantially in the vapor state and contains HF and light ASO;

partially condensing said stripper overhead stream to thereby form a liquid phase, containing light ASO, and a vapor phase, containing HF; and adding said vapor phase to said alkylation catalyst phase.

2. A method as recited in claim 1 wherein the concentration of ASO reaction by-product in the alkylation catalyst phase is in the range of from about 0.25 weight percent to about 10 weight percent and wherein the weight ratio of hydrogen fluoride to sulfone in the alkylation catalyst phase is in the range of from about 1:1 to about 40:1.

3. A method as recited in claim 2 wherein said vapor phase contains less than 5 weight percent light ASO.

4. A method as recited in claim 3 wherein said liquid phase further contains water and less than 50 weight percent HF.

5. A method as recited in claim 4 wherein said stripper bottoms stream further contains sulfone and less than 20 percent HF.

6. A method as recited in claim 5 wherein said sulfone is sulfolane.

7. A method as recited in claim 6 wherein said vapor phase is substantially free of light ASO.

* * * * *